(12) United States Patent
Zhang et al.

(10) Patent No.: US 6,527,943 B1
(45) Date of Patent: Mar. 4, 2003

(54) FUEL CELL CONCENTRATION SENSOR

(75) Inventors: Jiujun Zhang, Richmond (CA); Kevin M. Colbow, North Vancouver (CA); David P. Wilkinson, North Vancouver (CA); Jens Müller, Ulm (DE)

(73) Assignee: Ballard Power Systems, Inc., Burnaby (CA)

( * ) Notice: Subject to any disclaimer, the term of this patent is extended or adjusted under 35 U.S.C. 154(b) by 0 days.

(21) Appl. No.: 09/435,977

(22) Filed: Nov. 8, 1999

(51) Int. Cl.$^7$ ............................................. G01N 27/406
(52) U.S. Cl. ....................... 205/787; 204/422; 204/431; 429/30
(58) Field of Search ................................. 204/406, 418, 204/431, 432, 421, 422; 205/787; 429/30

(56) References Cited

U.S. PATENT DOCUMENTS

| | | | |
|---|---|---|---|
| 3,852,169 A | * 12/1974 | Kring et al. | 205/785.5 |
| 4,132,616 A | 1/1979 | Tantram et al. | |
| 4,362,789 A | * 12/1982 | Dighe | 429/17 |
| 4,770,026 A | * 9/1988 | Wolf | 73/23.3 |
| 4,810,597 A | 3/1989 | Kumagai et al. | |
| 5,497,753 A | 3/1996 | Kopera | |
| 5,624,538 A | 4/1997 | Luft et al. | |
| 5,738,773 A | * 4/1998 | Criddle et al. | 204/411 |
| 6,103,077 A | * 8/2000 | DeMarinis et al. | 204/290.07 |

FOREIGN PATENT DOCUMENTS

| | | |
|---|---|---|
| JP | 56-118273 | 9/1981 |
| WO | 98/45694 | 10/1998 |
| WO | WO 00/46869 | 8/2000 |

OTHER PUBLICATIONS

Gillespie et al "Chemistry", 1986, month unknown, Allyn and Bacon, pp. 68–70.*
Hong et al., "Fabrication of Polymer Electrolyte Fuel Cell (PEFC) H2 Sensors," *Sensors and Actuators, B 32, pp. 7–13*, Apr., 1996.
Ang et al. "A Simple Miniaturized Methanol–feed Control for Fuel Cells" *Energy Conversion, 12*:65–68 (1972) Month N/A.
Ciprios, "Session on Fuel Cell Battery System Methanol Fuel Cell Battery" *Proceedings: 20$^{th}$ Annual Power Sources Conference*, p 46–49 (May, 1966).
Barton, et al., "A Methanol Sensor for Portable Direct Methanol Fuel Cells" *J. Electrochem, Soc. 145*:(11)3783–3788 (Nov., 1998).
Criddle, et al., "Fuel Cell Sensors" *Selective Electrode Rev., 14*:195–223 (1992) Month N/A.

* cited by examiner

Primary Examiner—Robert J. Warden, Sr.
Assistant Examiner—Kaj K. Olsen
(74) Attorney, Agent, or Firm—McAndrews, Held & Malloy, Ltd.

(57) ABSTRACT

The measuring range of a fuel cell based concentration sensor can be extended by decreasing the load across the fuel cell terminals and by increasing the amount of oxidant supplied to the fuel cell. In this way, such a sensor avoids saturation, for example, when measuring methanol concentrations from 0 M to over 4 M in liquid aqueous solution. Such a sensor is suitable for use in measuring fuel concentrations in the recirculating fuel stream of certain fuel cell stacks (for example, direct methanol fuel cell stacks).

24 Claims, 7 Drawing Sheets

FUEL CELL CONCENTRATION SENSOR

FIELD OF THE INVENTION

The present invention relates to fuel cell based concentration sensors and extending the measuring range thereof. Further, it relates to methanol concentration sensors suitable for use in direct methanol fuel cell systems.

BACKGROUND OF THE INVENTION

Fuel cells have been used as sensors for measuring the concentration of various oxidizable species in gas or liquid mixtures. An important application has been in the determination of methanol content in breath samples or in the headspace above beer and/or wine during fermentation processes. Generally, the operation of fuel cell based sensors involves supplying the fluid mixture to be analyzed to the fuel cell anode and then measuring the electrical output of the fuel cell. No external potential or current is supplied to the sensor and the measured electrical output is typically proportional to the concentration of the oxidizable species present in the mixture.

Fuel cell systems have also been used historically as power supplies in certain specialized applications but are receiving increased attention of late for use in more general applications, including power supplies for various portable, motive, and stationary applications. In some fuel cell systems, it is necessary to determine the concentration of oxidizable species in certain fluid mixtures and thus it may be useful to employ a fuel cell sensor as a component in the fuel cell based power supply.

In general, electrochemical fuel cells convert reactants, namely fuel and oxidants, to generate electric power and reaction products. Electrochemical fuel cells employ an electrolyte disposed between two electrodes, namely a cathode and an anode. A solid polymer fuel cell is a specific type of fuel cell that employs a membrane electrode assembly ("MEA") which comprises a solid polymer electrolyte or ion-exchange membrane disposed between the two electrode layers. An electrocatalyst is needed to induce the desired electrochemical reactions at the electrodes. The electrocatalyst used may be a metal black, an alloy or a supported metal catalyst, for example, platinum on carbon. The electrocatalyst is typically incorporated at the electrode/electrolyte interfaces. This can be accomplished, for example, by depositing it on a porous electrically conductive sheet material, or "electrode substrate", or on the membrane electrolyte. Flow field plates for directing the reactants across one surface of each electrode substrate are generally disposed on each side of the MEA. Solid polymer fuel cells typically operate in a range from about 40° C. to about 150° C.

A broad range of reactants has been contemplated for use in solid polymer fuel cells and such reactants may be delivered in gaseous or liquid streams. The oxidant may, for example, be substantially pure oxygen or a dilute oxygen stream such as air. The fuel stream may, for example, be substantially pure hydrogen gas, a gaseous hydrogen-containing reformate stream derived from a suitable feedstock, or a suitable gaseous or liquid organic fuel mixture. Liquid feedstocks and/or fuels, such as methanol, are preferred, particularly in non-stationary applications, since they are relatively easy to store and handle. Where possible, it is advantageous to react a fuel mixture directly in the fuel cell (that is, to supply the fuel unreformed to the fuel cell anodes) in order to avoid using a reformer in the fuel cell system. Inside the fuel cell, the fuel mixture may be reacted electrochemically (directly oxidized) to generate electricity or instead it may be reformed in-situ (internally reformed), as in certain high temperature fuel cells (for example, solid oxide fuel cells).

A direct methanol fuel cell (DMFC) is a type of solid polymer fuel cell that operates directly on a methanol fuel stream typically supplied as a methanol/water vapor or as an aqueous methanol solution in liquid feed DMFCs. The methanol in the fuel stream is directly oxidized at the anode therein. There is often a problem in DMFCs with crossover of methanol fuel from the anode to the cathode side through the membrane electrolyte. The methanol that crosses over typically then reacts with oxidant at the cathode and cannot be recovered, resulting in significant fuel inefficiency and deterioration in fuel cell performance. To reduce crossover, very dilute solutions of methanol (for example, about 5% methanol in water) are typically used as fuel streams in liquid feed DMFCs. The fuel streams in DMFCs are usually recirculated in order to remove carbon dioxide (a by-product of the reaction at the anode) and to re-use the diluent and any unreacted fuel in the depleted fuel stream exiting the DMFC). Methanol is added to the circulating fuel stream before it re-enters the fuel cell in order to compensate for the amount consumed, thereby providing a fresh mixture at the desired methanol concentration. Since the amount of methanol consumed is variable (depending on the load, crossover, and other operating parameters), the methanol concentration in the circulating fuel stream is usually measured continuously with a suitable sensor, and fresh methanol is admitted in accordance with the signal from the sensor.

Various types of sensors may be considered for purposes of measuring the concentration of methanol in aqueous solution and thus for use in a recirculating fuel stream in a liquid feed DMFC. For instance, a fuel cell based sensor may be considered. In Japanese Published Patent Application No. 56-118273, a small capacity, temperature-compensated fuel cell is suggested for use as a concentration sensor for a liquid electrolyte air-methanol fuel cell. A signal from the sensor is obtained by measuring the voltage across a large resistance connected across the small capacity fuel cell. In "Fuel Cell Sensors", Selective Electrode Rev., 1992, Vol. 14, pp. 125–223, W. J. Criddle et al. discuss the principles and applications of fuel cell sensors generally. It was noted that diffusion from the air is usually sufficient for the oxygen supply in fuel cell sensors. Thus in principle, as long as the species concentration to be measured is in an appropriate range, a conventional direct methanol fuel cell may be employed as the concentration sensor. Saturation of such a sensor (where the electrical output of the sensor levels off and the sensor is no longer responsive to an increase in concentration) may occur however at higher methanol concentrations.

A fuel cell based concentration sensor for use in DMFCs is disclosed in U.S. Pat. No. 5,624,538. Therein, an additional, diffusion limiting, membrane is employed against the side of the anode opposite the ion conducting membrane electrolyte in the sensor fuel cell. The diffusion limiting membrane is used to limit the transport of methanol. It was suggested that the measuring range of this sensor could be expanded by varying the thickness of the diffusion limiting membrane.

Other types of sensors include capacitance devices or amperometric devices. The former measure the change in dielectric constant of the fuel stream with methanol concentration. The latter measure the current output from electrochemical cells in which an external potential is applied across the electrochemical cells and current is generated in accordance with the species concentration. The devices described in PCT/International Publication No. WO 98/45694 (Application No. PCT/US98/07244) and J. Electrochem. Soc., Vol. 145, No. 11, Nov. 1998, p. 3783 are examples of the latter. Along with an electrical meter for measuring the output of these devices, an additional apparatus is required to apply an external potential.

A preferred sensor however would measure methanol concentration over an extended range, without saturating at the higher methanol concentrations of interest, and without requiring an external power supply.

SUMMARY OF THE INVENTION

The present invention provides for extending the measuring range of a fuel cell based sensor that measures the concentration of an oxidizable species in a gaseous or liquid fluid mixture. This is accomplished by decreasing the load applied across the fuel cell terminals and by increasing the oxidant supply such that saturation of the sensor fuel cell electrical output is avoided over the extended measuring range. A sensor with such an extended range is particularly suited for use in DMFC systems because, in many circumstances, the construction and/or operating conditions of conventional DMFCs are such that they are not capable of measuring methanol concentration over a satisfactory range for the purposes of the DMFC system. In conventional direct methanol fuel cell types, the electrical output of the sensor can become saturated at high methanol concentrations, thereby rendering the sensor ineffective in that range.

The concentration sensor comprises a solid polymer fuel cell in which the oxidizable species can be directly oxidized, a load across the terminals of the fuel cell, and an electrical meter for measuring an electrical output of the fuel cell. The fuel cell comprises an anode electrode supplied with the fluid mixture comprising the oxidizable species, a cathode electrode supplied with an oxidant at an oxidant stoichiometry, and a solid polymer electrolyte. (Oxidant stoichiometry is defined as the ratio of the rate oxidant is supplied to the cathode to that consumed in the electricity generating reaction of the fuel cell.) Any oxidant that reacts with crossed over species at the cathode is not included in the amount consumed since no useful external electricity is generated.) The oxidizable species may be an alcohol (for example, methanol), an ether (for example, dimethyl ether), an aldehyde, or an ester. In particular, the fluid mixture may be a liquid aqueous methanol solution and the fuel cell may be a direct methanol fuel cell. The operating temperature of the fuel cell may preferably be between about 40° C. and 100° C.

To extend the measuring range of the sensor, the load across the fuel cell terminals is decreased thereby increasing the current density in the fuel cell. The electrochemical consumption of the oxidizable species at the anode is thus increased, which in turn can result in a diffusion limited situation for the species within the anode, thereby avoiding saturation. Additionally, less of the species is available to crossover the electrolyte membrane to the cathode and thus adverse effects due to crossover are reduced. (Once the oxidizable species has crossed over to the cathode, it can compete for and react with the oxidant intended for electrochemical reaction with already oxidized (that is, measured) species. Further, this competing reaction lowers the cathode potential.) In a methanol concentration sensor, an extended measuring range may be obtained by decreasing the load across the fuel cell terminals to less than about 10 ohms. The range can be extended further by decreasing the load across the fuel cell terminals to less than about 10 milliohms.

The oxidant stoichiometry is also increased to suppress oxidant mass transport limitations. A sensor having extended measuring range may operate at an oxidant stoichiometry greater than about 2 and thus would include oxidant supply means capable of supplying the sensor's fuel cell at that stoichiometry. A conventional apparatus may be used to supply the increased oxidant. Conveniently, if the sensor is used as a component in a power supply comprising a direct oxidation fuel cell stack, the source of the oxidant supplied to the cathode of the sensor's fuel cell may be the same as that supplied to the direct oxidation fuel cell stack.

With a suitable choice of load and oxidant stoichiometry, the measuring range of a methanol concentration sensor can be extended to measure methanol concentrations from 0 M to 4 M in liquid aqueous methanol solution. The measured electrical output of the fuel cell in the sensor may be essentially proportional to the methanol concentration over the range 0 M to 2 M, thus providing a linear response to concentration. It may be advantageous to provide means for varying the load and/or the rate of oxidant supply during operation of the concentration sensor such that its measuring range may be varied during operation.

The electrical output measured may be either the current through the load or the voltage across the load. Thus, the electrical meter in the sensor may be either an ammeter or a voltmeter.

Preferably, the sensor is relatively small since this provides several advantages including superior response times. For instance, the area of the electrodes in the sensor's fuel cell may be less than about 1 cm$^2$. A flow field plate for such a miniature fuel cell can be of simple construction, for instance comprising a single flow channel.

A concentration sensor of the invention is particularly suited for use in a power supply comprising a fuel cell stack supplied with a recirculating fuel stream, for example, a DMFC stack. The sensor is used to measure the concentration of the oxidizable species in the recirculating fuel stream and to direct the operation of a device that adjusts the concentration of the oxidizable species in the recirculating fuel stream.

DETAILED DESCRIPTION OF PREFERRED EMBODIMENTS

Figure 1:
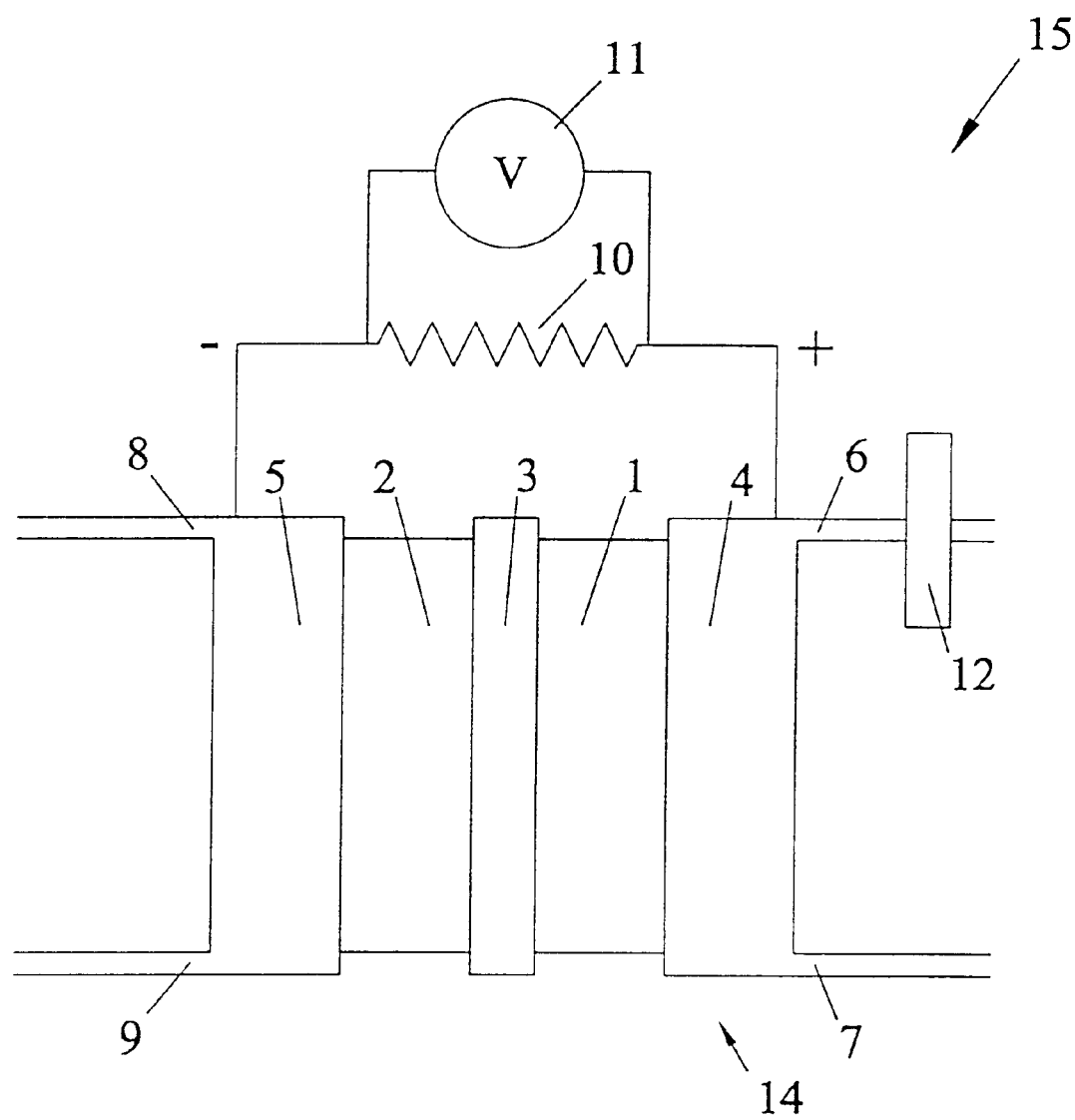
FIG. 1 shows a schematic diagram of a concentration sensor comprising a miniature solid polymer fuel cell.

A preferred embodiment of a concentration sensor 15 based on a solid polymer fuel cell is shown schematically in FIG. 1. The fuel cell 14 includes cathode electrode 1, anode electrode 2, and polymer electrolyte membrane 3. Oxidant flow field plate 4 and fuel flow field plate 5 are used to distribute air and fuel reactants to the cathode 1 and anode 2 respectively. For a small size concentration sensor, a single flow channel formed in each flow field plate 4, 5 may be sufficient to distribute the reactants. Air is supplied to the oxidant flow field plate 4 at oxidant inlet 6 and exhausts at oxidant outlet 7. The fluid mixture comprising the oxidizable species to be measured is supplied to fuel flow field plate 5 at fuel inlet 8 and exhausts at fuel outlet 9. A resistor 10 is connected as a fixed load across the terminals of the fuel cell 14 and an electrical output of the fuel cell is measured. In this case the voltage across resistor 10 is measured with voltmeter 11. Resistor 10 may optionally be a variable resistor. An ammeter in series with resistor 10 may be used instead of voltmeter 11 to measure electrical output of the fuel cell. To avoid saturating the sensor at high species concentrations and to obtain an extended measuring range, concentration sensor 15 has a lower load, in this case resistor 10, and operates at a greater oxidant stoichiometry than known sensors. As shown in FIG. 1, greater oxidant stoichiometry may be achieved through use of a fan 12 which forces air flow through oxidant flow field plate 4 via inlet 6 and outlet 7. Various other conventional means may be employed however to achieve increased operating oxidant stoichiometry. Under these conditions, the electrical output of the sensor may be essentially proportional to the species concentration over the extended range and calibration of the sensor is simplified. (A non-linear part of the measuring range may also be employed, but then calibration is more difficult. Aside from species concentration, the electrical output of the sensor may also depend on various other parameters such as load, temperature, and other operating parameters as shown in the Examples described below.)

Prior art fuel cell based sensors typically employ a relatively large load across the fuel cell terminals. Further, such sensors typically do not require nor employ a substantial supply of oxidant. Oxidant supply is often obtained by exposing the cathode to air and relying on diffusion and/or convection. In such cases, oxidant stoichiometry is the ratio of the rate at which oxidant reaches (that is, is supplied to) the surface of the cathode by diffusion and/or convection to that consumed in the electrochemical reaction at the cathode. (Note that in determining stoichiometry in fuel cells with practical oxidant flow field plates, the rate at which oxidant is supplied to the cathode is simply considered to be the rate at which oxidant enters the flow field plate. It is assumed that all the oxidant entering reaches the cathode.)

A low load across the terminals of fuel cell 14 is achieved via use of an appropriate resistor 10. For instance, a resistor less than about 10 ohms may be used in order to extend the measuring range for methanol to over 1 M in an aqueous methanol solution. Further, a resistor less than about 10 milliohms may be used in order to extend the measuring range for methanol to over 2 M.

In the embodiment comprising an oxidant flow field plate 4 as shown in FIG. 1, increased oxidant stoichiometry is obtained by flowing air therethrough using an appropriately selected fan 12 or via other conventional means. For instance, an oxidant stoichiometry greater than about 4 may be used in order to extend the measuring range for methanol in an aqueous methanol solution. It is also possible to increase the oxidant stoichiometery in embodiments without a flow field plate. For instance, if the cathode is open to the surrounding air, oxidant stoichiometry can be increased via forced convection, for example, blowing air over the exposed cathode using a fan.

When the species concentration at the sensor anode is high enough, a saturation condition may exist in which the sensor output will no longer indicate changes in concentration. The use of a lower load however results in higher current densities in the fuel cell and can instead lead to a diffusion limited situation for the species within the anode. If so, saturation at the anode is avoided and the measurement range can be extended. Further, when significant crossover of the species can occur in the sensor cell, such crossover can adversely limit the capability of the sensor. However, operation at higher current densities reduces the species concentration in the vicinity of the polymer electrolyte and thus advantageously reduces crossover.

Oxidant stoichiometry is increased to provide ample oxidant in order to avoid oxidant mass transport limitations at the cathode. Thus, there is always sufficient oxidant to completely react with species oxidized at the anode and with any species that may have crossed over the membrane electrolyte. Further, an ample flow of oxidant is useful in that it can eliminate any chance of flooding in the cathode flow field plate and/or electrode again avoiding oxidant mass transport limitations.

The concentration sensor is preferably small in size, partly to simplify construction and reduce cost, but also to enhance performance. Use of a smaller fuel cell therein can reduce the sensor's response time (since changeover of the volume to be sampled in the smaller fuel cell is more rapid). Preferably therefore, the area of the fuel cell electrodes is less than about 1 cm$^2$.

The electrical output of the fuel cell in the sensor will vary with temperature and thus temperature control of the sensor is required. For a DMFC based concentration sensor, preferred operating temperatures are in the range between about 40° C. and 100° C. For purposes of temperature control, many conventional methods may be used for sensor heating, cooling, and temperature measurement. For instance, heating might be provided via an electric heater element embedded in a flow field plate in the sensor. Cooling might be provided, where appropriate, using the cooling fan that provides the oxidant supply. A standard thermocouple may be used to indicate sensor temperature and a control circuit may be used to control temperature based on the sensed temperature.

A preferred application for an extended range concentration sensor is in fuel cell based power supplies which employ recirculating fuel streams, for example, a DMFC based power supply. The sensor measures the concentration of the fuel component in the recirculating fuel stream and directs the operation of a device that adjusts the fuel concentration in the fuel stream supplied to the DMFC. In DMFCs, the typical recirculating fuel stream comprises a dilute solution of methanol in water. However, as technology progresses (for example, with the possible discovery of improved membranes with reduced methanol crossover characteristics), the operating concentration of methanol used in the recirculating fuel mixtures may be expected to increase, and thus sensors for even higher concentrations may be desirable.

Although a typical fuel cell based power supply operates at lower oxidant stoichiometries than a preferred concentration sensor, the oxidant needed for a small, extended range sensor is generally insignificant compared to that used in the fuel cell stack in the power supply. (A typical fuel cell based power supply operates at oxidant stoichiometries less than about 2 typically in order to minimize parasitic power losses incurred in supplying oxidant. Such parasitic power losses are not a significant concern in a tiny sensor.) Thus, a convenient source of oxidant for the concentration sensor is the same as that for the fuel cell stack in the power supply. Further, since the temperature of the recirculating fuel stream is often controlled at certain points, suitable temperature control of the sensor may possibly be obtained via contact with the fuel stream. Alternatively, there are usually various sources of heat or cold from components in the power supply that may be used to control the sensor temperature.

The following examples pertain to measuring methanol concentrations in aqueous solutions and have been included to illustrate different embodiments and aspects of the invention but these should not be construed as limiting in any way.

Concentration Sensor Examples

A miniature solid polymer fuel cell sensor was constructed as generally depicted in FIG. 1. The anode and cathode comprised unsupported platinum/ruthenium and platinum catalysts respectively on TGP carbon fiber paper substrates (product from Toray). The electrodes were about 1 cm long by 0.5 cm wide. The membrane electrolyte employed was Nafion™ 117. Each flow field plate was made out of graphite and had a single, central, straight fluid channel (approximately 1 mm wide) milled over its length. The fuel cell sensor was operated using air as the oxidant stream. Several liquid aqueous methanol mixtures were supplied as fuel streams at 1 bar absolute pressure. In the following tests, the current through the load was measured, rather than the voltage as shown in FIG. 1.

Figure 2:
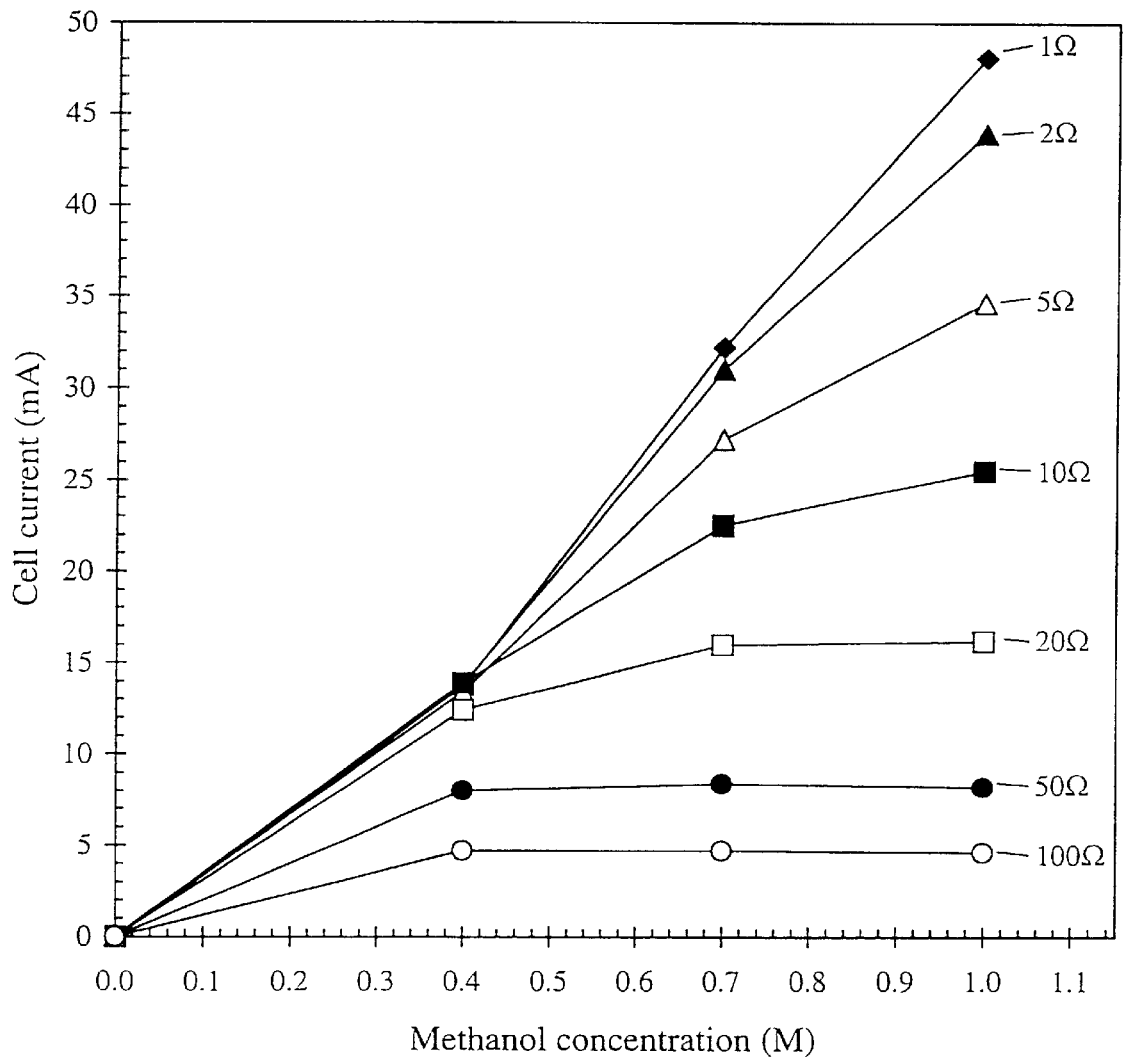
FIG. 2 shows the fuel cell current output versus methanol concentration in an exemplary sensor using different fixed load resistances connected across the fuel cell.

FIG. 2 shows the current output from the fuel cell sensor versus methanol concentration in the fuel stream using different fixed load resistances. Here, air was supplied at 3 bar absolute pressure and the fuel cell temperature was maintained at 50° C. The fuel and air flow rates through the cell were 2 mL per minute and 37 mL per minute respectively. This corresponds to an oxidant stoichiometry of about 130 at the highest current, 50 mA. For load resistors of about 20 ohms and up, the current output from the fuel cell sensor appears saturated at concentrations below 1 M. However, using the lower load resistors, current output is roughly proportional to methanol concentration up to at least 1 M.

Figure 3:
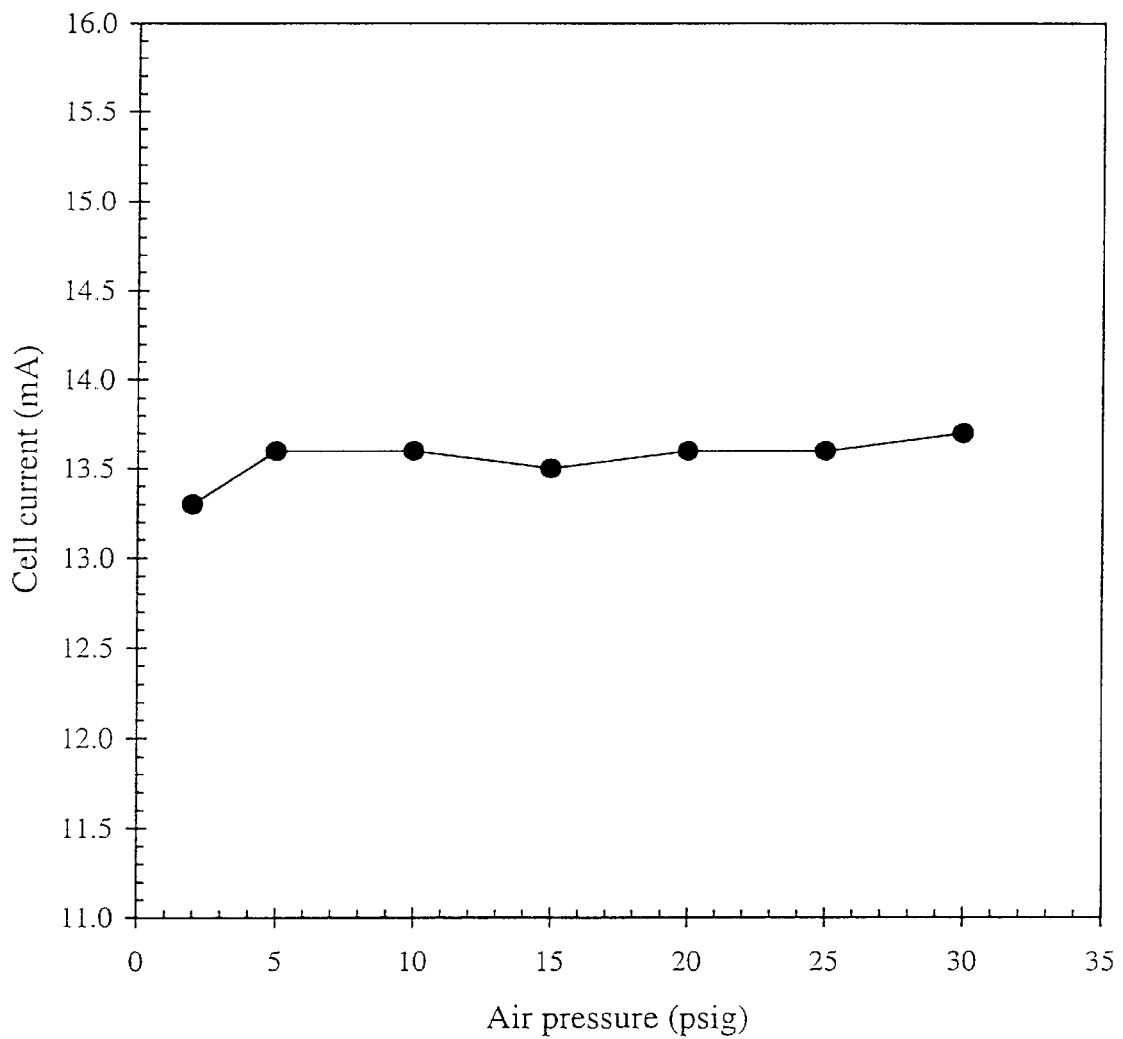
FIG. 3 shows the dependence of output current on air pressure in an exemplary sensor.

The air supply pressure in the same fuel cell sensor was then varied to determine the sensitivity of the sensor output to air pressure variations. Here, a 5 ohm load resistor and a 0.4 M methanol fuel solution was used. FIG. 3 shows the current versus air pressure results. The current output is relatively insensitive to air pressure under these conditions.

Figure 4:
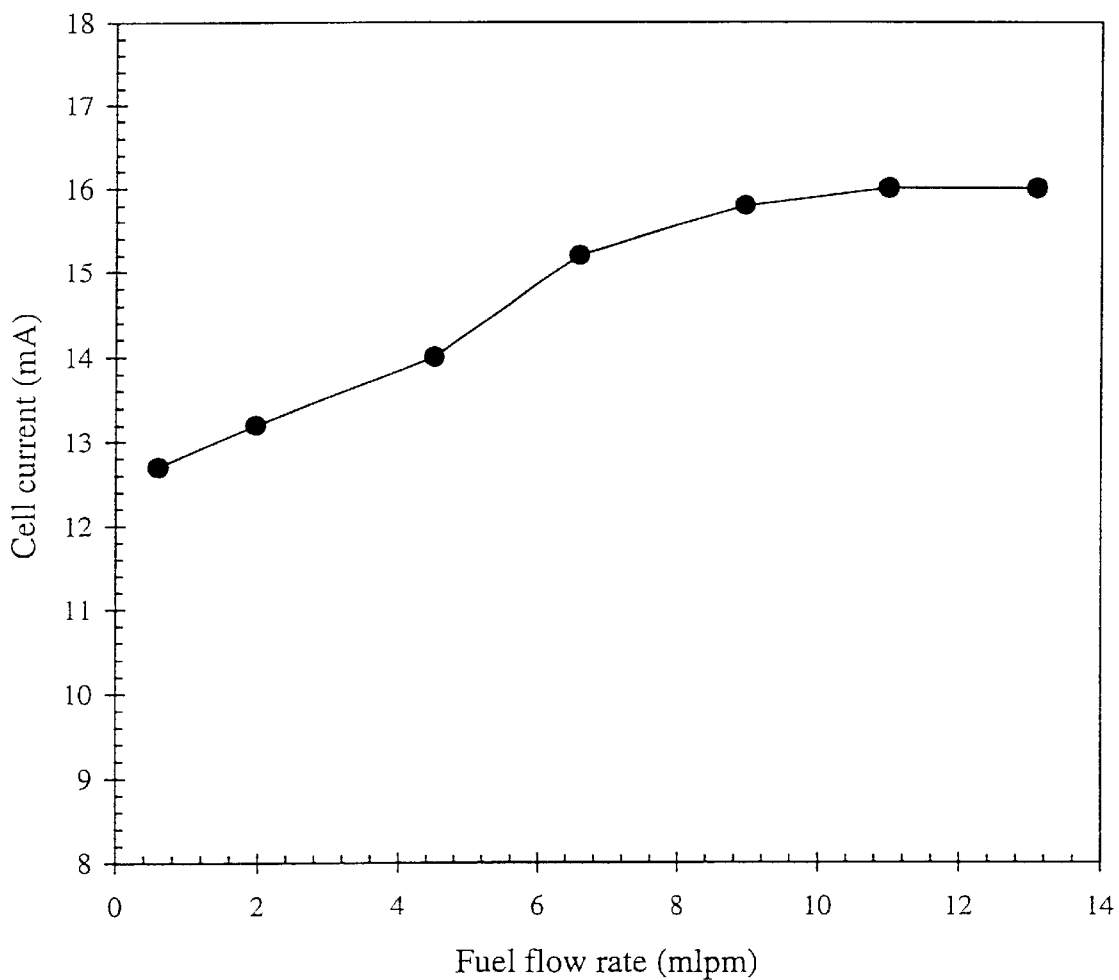
FIG. 4 shows the dependence of output current on fuel flow rate in an exemplary sensor.

Next, the fuel flow rate was varied to determine the sensitivity of the sensor output to fuel flow rate variations. Again, a 5 ohm load resistor and a 0.4 M methanol fuel solution was used. FIG. 4 shows the current versus fuel flow rate results. The output current shows only a slight dependence on the fuel flow rate under these conditions.

Figure 5:
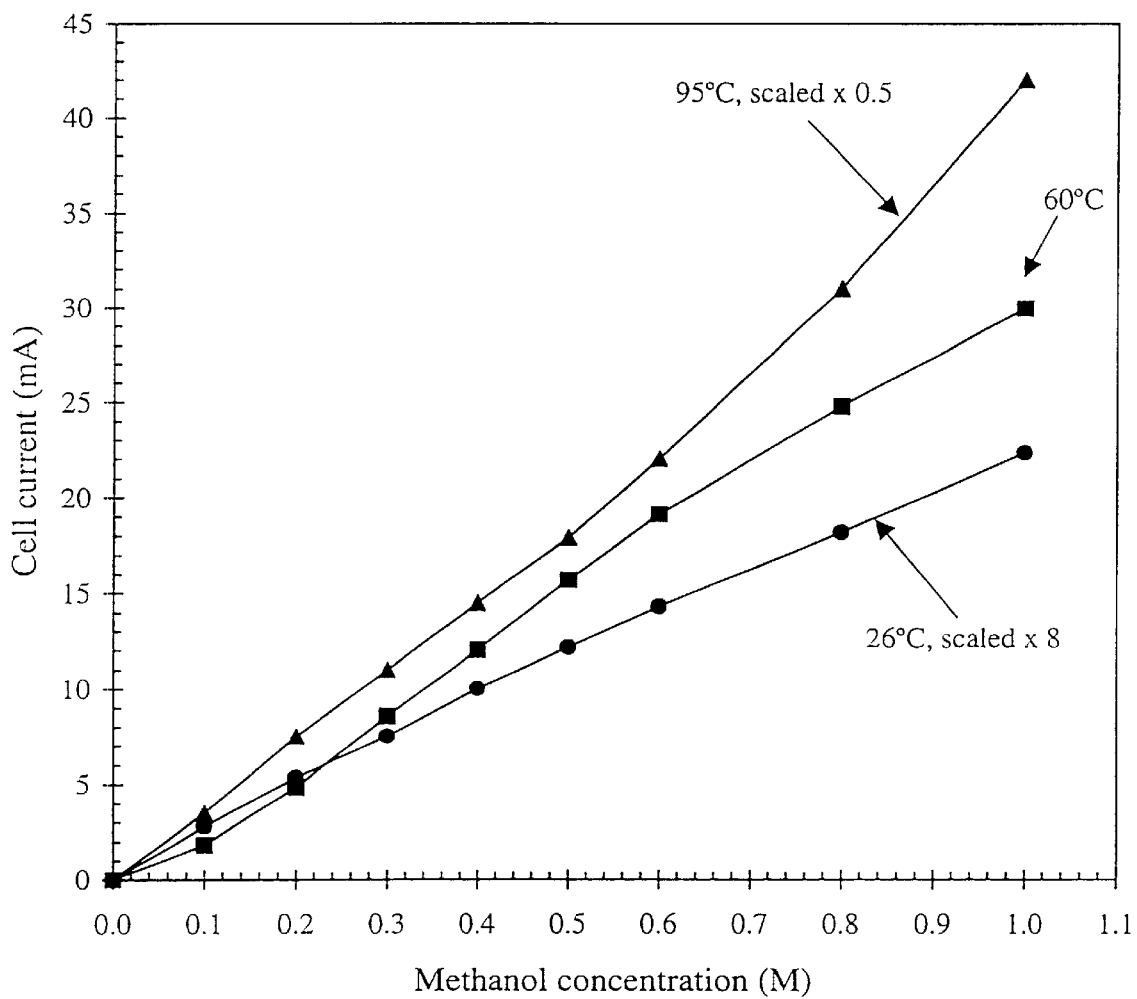
FIG. 5 shows the dependence of output current on temperature in an exemplary sensor.

FIG. 5 illustrates the temperature dependence of the sensor output. Current is again plotted versus methanol concentration at three different temperatures (26, 60, and 95° C.). A 10 ohm load resistor was used at the former two temperatures and a 2 ohm resistor at the latter temperature. Essentially linear behavior is observed at all temperatures, but there is a substantial difference in the magnitude of the current. For purposes of comparison on the same figure, note that the current values in the 26° C. plot have been multiplied by a factor of 8 and the values in the 95° C. plot have been multiplied by a factor of 0.5, in FIG. 5.

Figure 6:
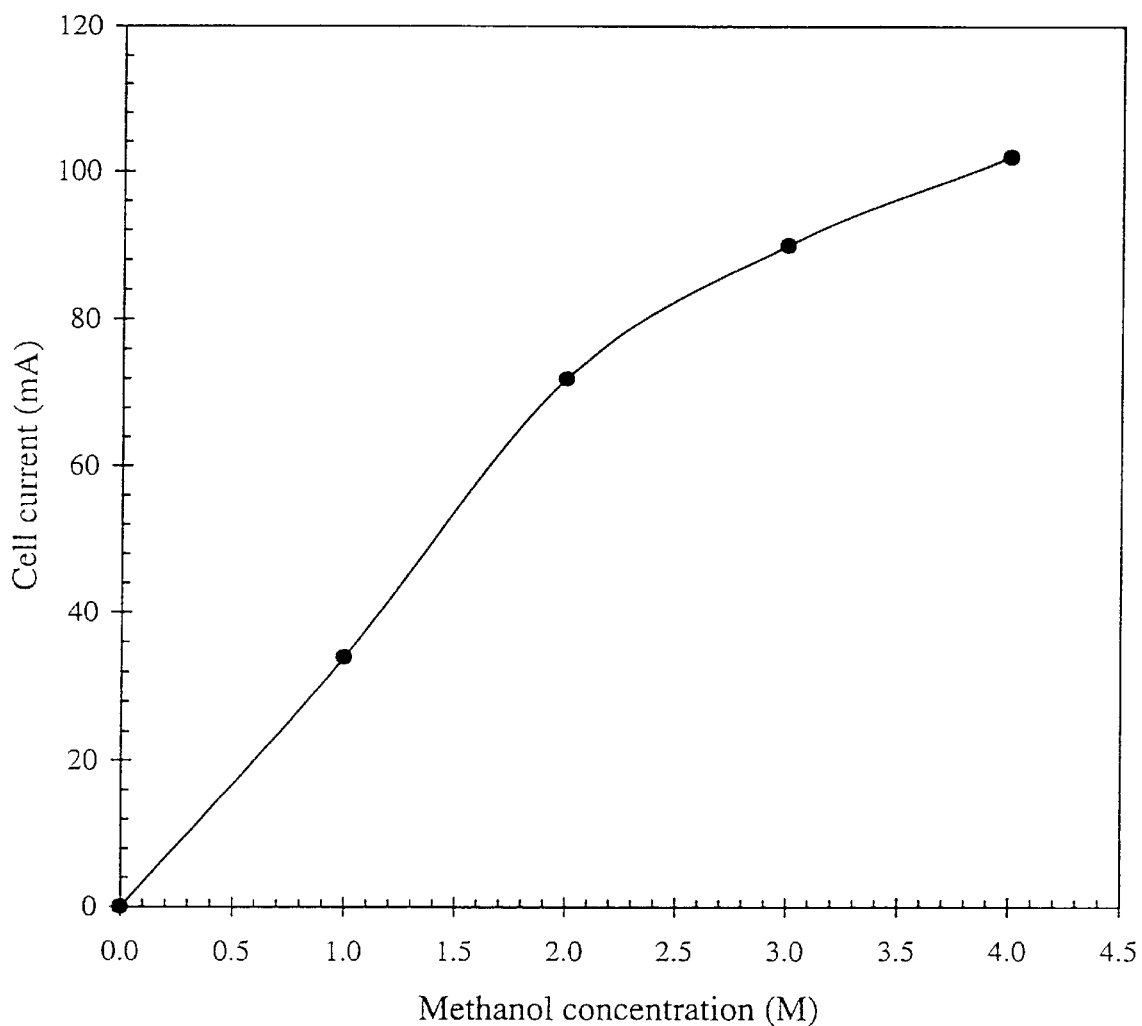
FIG. 6 shows the fuel cell current output versus methanol concentration in an exemplary sensor using a very low load resistance.

The same fuel cell sensor was then operated at a temperature of 50° C. with fuel and air flow rates of about 0.6 mL per minute and 220 mL per minute, respectively. A load resistor of only 5 milliohms was used this time and again current output versus methanol concentration was determined as shown in FIG. 6. The oxidant stoichiometry here was about 760 at the highest current, 50 mA. Under these conditions, the sensor output is roughly linear with respect to methanol concentrations up to about 2 M.

In the determination of the data in the preceding figures where the fuel cell sensor was subjected to discrete changes in methanol concentration, response times of 10 second to 20 second to about 95% current were observed. It is expected that this response time can be improved by reducing sensor size and/or flow field channel depth.

Figure 7:
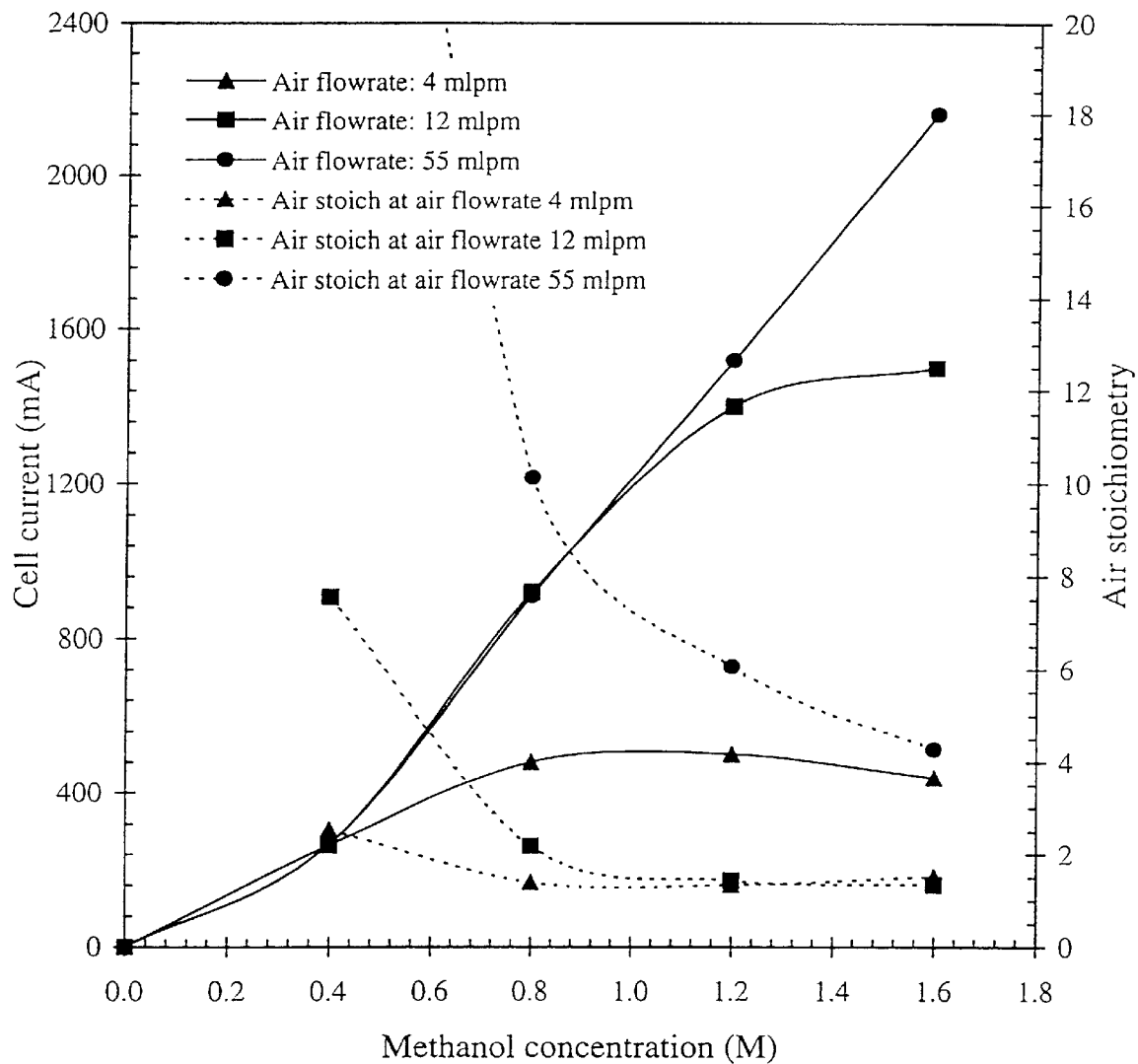
FIG. 7 shows the dependence of output current on air flow rate in an exemplary sensor. Oxidant stoichiometry is also shown.

Another solid polymer fuel cell sensor was constructed as in the preceding description except that the active electrode area was about 6 cm$^2$. The fuel cell output was then determined as a function of methanol concentration at different oxidant flow rates. Here, the fuel cell sensor temperature was 50° C. Air was used as the oxidant stream at 1 bar absolute pressure. Several liquid aqueous methanol mixtures were supplied as fuel streams at 1 bar absolute pressure and a flow rate of about 0.6 mL per minute. A 5 milliohm load resistor was used across the fuel cell terminals. FIG. 7 shows the current output versus methanol concentration in the fuel stream at three different air flow rates (4, 12, and 55 mL per minute). The air stoichiometries are also plotted in FIG. 7 for each current versus concentration datapoint at a given flow rate. FIG. 7 shows that the range of the sensor is extended by using higher oxidant flow rates. Non-linearity begins to appear in the 12 mL per minute air flow rate data for fuel mixtures above 0.8 M. Likewise, non-linearity begins to appear in the 4 mL per minute air flow rate data for fuel mixtures above 0.4 M. These points correspond to air stoichiometries below or about 2.

While particular elements, embodiments and applications of the present invention have been shown and described, it will be understood, of course, that the invention is not limited thereto since modifications may be made by those skilled in the art without departing from the spirit and scope of the present disclosure, particularly in light of the foregoing teachings.

What is claimed is:

1. A method of operating a sensor over a measuring range, said sensor measuring the concentration of an oxidizable species in a fluid mixture, said sensor comprising a solid polymer fuel cell in which said oxidizable species can be directly oxidized, a load across the terminals of said fuel cell, and an electrical meter for measuring an electrical output of said fuel cell, said fuel cell comprising an anode electrode directly supplied with said fluid mixture, a cathode electrode supplied with an oxidant at an oxidant stoichiometry, and a solid polymer electrolyte, wherein said fuel cell does not include a diffusion-limiting membrane operably linked to said anode electrode on the anode side opposite said solid polymer electrolyte, said method comprising:

decreasing said load across said terminals of said fuel cell, wherein said decreased load is less than about 10 ohms; and increasing said oxidant stoichiometry, wherein said increased oxidant stoichiometry is greater than about 2, whereby saturation of said fuel cell electrical output is avoided over said measuring range.

2. The method of claim 1 wherein said oxidizable species is selected from the group consisting of an alcohol, an ether, an aldehyde, and an ester.

3. The method of claim 2 wherein said oxidizable species is methanol.

4. The method of claim 3 wherein said fluid mixture is a liquid aqueous methanol solution.

5. The method of claim 4 wherein said fuel cell is a direct methanol fuel cell.

6. The method of claim 5 wherein said decreased load across said terminals of said fuel cell is less than about 10 ohms.

7. The method of claim 6 wherein said decreased load across said terminals of said fuel cell is less than about 10 milliohms.

8. The method of claim 5 wherein the area of said electrodes is less than about 1 cm$^2$.

9. The method of claim 5 wherein the operating temperature of said direct methanol fuel cell is between about 40° C. and 100° C.

10. The method of claim 5 wherein said measuring range of said concentration sensor is extended to measure a methanol concentration from 0 M to at least 2 M in said liquid aqueous methanol solution.

11. The method of claim 10 wherein said measuring range of said concentration sensor is extended to measure a methanol concentration from 0 M to at least 4 M in said liquid aqueous methanol solution.

12. The method of claim 10 wherein said electrical output of said fuel cell is essentially proportional to said methanol concentration over said range.

13. The method of claim 1 wherein said meter is an ammeter and said electrical output of said fuel is the current through said load.

14. The method of claim 1 wherein said meter is a voltmeter and said electrical output of said fuel is the voltage across said load.

15. A method of operating a methanol concentration sensor that measures the concentration of methanol in a fluid mixture, said concentration sensor comprising a solid polymer fuel cell in which methanol can be directly oxidized, and an electrical meter for measuring an electrical output of said fuel cell, said fuel cell comprising an anode electrode directly supplied with said fluid mixture, a cathode electrode, and a solid polymer electrolyte, wherein said fuel cell does not include a diffusion-limiting membrane operably linked to said anode electrode on the anode side opposite said solid polymer electrolyte, said method comprising:

connecting a load less than about 10 ohms across the terminals of said fuel cell; and supplying oxidant to said cathode electrode, at an oxidant stoichiometry greater than about 2, whereby said fuel cell electrical output is limited by said methanol concentration at least up to 2 M.

16. The method of claim 15 further comprising:

connecting a sufficiently low load across the terminals of said fuel cell; and supplying sufficient oxidant to said cathode electrode, such that said fuel cell electrical output is limited by said methanol concentration at least up to 4 M.

17. The method of claim 15 further comprising varying one of said load and said oxidant supply during operation of said concentration sensor, such that the measuring range of said concentration sensor is varied during operation.

18. A sensor for measuring the concentration of an oxidizable species in a fluid mixture comprising:

a solid polymer fuel cell comprising an anode electrode, a cathode electrode, and a solid polymer electrolyte, and wherein said fuel cell does not include a diffusion-limiting membrane operably linked to said anode electrode on the anode side opposite said solid polymer electrolyte;

means for supplying oxidant to said cathode electrode at an oxidant stoichiometry of greater than about 2;

a load connected across the terminals of said fuel cell of less than about 10 ohms; and an electrical meter for measuring an electrical output of said fuel cell.

19. The concentration sensor of claim 18 wherein said oxidizable species is methanol.

20. The concentration sensor of claim 18 wherein the area of said fuel cell electrodes is less than about 1 cm$^2$.

21. The concentration sensor of claim 18 wherein said fuel cell comprises a flow field plate comprising a single flow channel.

22. A power supply comprising a fuel cell stack supplied with a recirculating fuel stream; a device for adjusting the concentration of an oxidizable species in said recirculating fuel stream; and a concentration sensor located in said recirculating fuel stream for measuring the concentration of said oxidizable species therein and for directing the operation of said concentration adjusting device, wherein said concentration sensor comprises:

a solid polymer fuel cell comprising an anode electrode, a cathode electrode, and a solid polymer electrolyte, and wherein said fuel cell does not include a diffusion-limiting membrane operably linked to said anode electrode on the anode side opposite said solid polymer electrolyte;

means for supplying oxidant to said cathode electrode at an oxidant stoichiometry of greater than about 2;

a load across the terminals of said fuel cell of less than about 10 ohms; and an electrical meter for measuring an electrical output of said fuel cell.

23. The power supply of claim 22 wherein said fuel cell stack is a direct methanol fuel cell stack and said oxidizable species is methanol.

24. The power supply of claim 22 wherein the source of the oxidant supplied to said fuel cell stack is the same as the source of the oxidant supplied to said cathode electrode of said polymer fuel cell.

* * * * *